US007816562B2

(12) United States Patent
Feng et al.

(10) Patent No.: US 7,816,562 B2
(45) Date of Patent: *Oct. 19, 2010

(54) AMIDO-ORGANOBORATE INITIATOR SYSTEMS

(75) Inventors: Shaoguang Feng, Midland, MI (US); Gary L. Jialanella, Oxford, MI (US); Peter Nickias, Midland, MI (US); Toni Ristoski, Rochester Hills, MI (US)

(73) Assignee: Dow Global Technologies Inc., Midland, MI (US)

( * ) Notice: Subject to any disclaimer, the term of this patent is extended or adjusted under 35 U.S.C. 154(b) by 572 days.

This patent is subject to a terminal disclaimer.

(21) Appl. No.: 11/544,521

(22) Filed: Oct. 6, 2006

(65) Prior Publication Data

US 2007/0083051 A1    Apr. 12, 2007

Related U.S. Application Data

(60) Provisional application No. 60/724,943, filed on Oct. 7, 2005.

(51) Int. Cl.
C08F 4/52      (2006.01)
C08F 265/06    (2006.01)

(52) U.S. Cl. .................. 564/9; 428/355; 428/411.1; 428/500; 428/515; 428/516; 428/520; 502/100; 502/150; 502/162; 502/200; 502/202; 526/89; 526/123.1; 526/131; 526/134; 526/195; 526/196; 526/197; 526/198; 526/201; 526/204; 526/217; 526/227; 526/235; 526/236; 526/317.1; 526/319; 526/328; 526/329.7; 548/100; 548/250; 548/255; 548/262.2; 548/300.1; 548/335.1; 548/356.1; 548/373.1; 548/400; 548/405; 548/406; 548/560; 548/564; 564/2; 564/8; 528/4; 528/5; 528/6; 528/7; 528/394; 528/422; 528/423; 528/44; 528/48; 528/52

(58) Field of Classification Search .......... 526/131, 526/134, 195, 196, 197, 198, 201, 204, 217, 526/218.1, 219.2, 227, 229, 230, 230.5, 235, 526/236, 317.1, 319; 508/158; 564/9
See application file for complete search history.

(56) References Cited

U.S. PATENT DOCUMENTS

| 3,236,823 A | 2/1966 | Leverkusen et al. |
| 3,275,611 A | 9/1966 | Mottus et al. |
| 3,527,737 A | 9/1970 | Masuhara et al. |
| 3,819,447 A | 6/1974 | Dailibor et al. |
| 3,890,407 A | 6/1975 | Briggs et al. |
| 3,971,751 A | 7/1976 | Isayama et al. |
| 4,104,450 A * | 8/1978 | Whitney et al. ............ 429/337 |
| 4,106,971 A | 8/1978 | Briggs et al. |
| 4,112,013 A | 9/1978 | Briggs et al. |
| 4,117,213 A * | 9/1978 | Whitney et al. ............ 429/337 |
| 4,344,800 A | 8/1982 | Lutz |
| 4,385,153 A | 5/1983 | Ritter |
| 4,426,243 A | 1/1984 | Briggs |
| 4,448,927 A | 5/1984 | Faloener et al. |
| 4,515,724 A | 5/1985 | Ritter |
| 4,536,546 A | 8/1985 | Briggs |
| 4,538,920 A | 9/1985 | Drake |
| 4,552,604 A | 11/1985 | Green |
| 4,676,858 A | 6/1987 | Ritter |
| 4,705,838 A | 11/1987 | Goel |
| 4,746,725 A | 5/1988 | Evans et al. |
| 4,773,957 A | 9/1988 | Briggs |
| 4,788,254 A | 11/1988 | Kawakubo et al. |
| 4,823,927 A | 4/1989 | Jensen |
| 4,920,188 A | 4/1990 | Sakashita |
| 4,921,921 A | 5/1990 | Ritter |
| 4,942,201 A | 7/1990 | Briggs et al. |
| 4,985,477 A | 1/1991 | Collins et al. |
| 4,985,516 A | 1/1991 | Sakashita et al. |
| 5,034,464 A | 7/1991 | Arduengo |
| 5,079,098 A | 1/1992 | Liu |
| 5,082,147 A | 1/1992 | Jacobs |
| 5,106,928 A | 4/1992 | Skoultchi et al. |
| 5,112,691 A | 5/1992 | Briggs et al. |
| 5,126,416 A | 6/1992 | Yang |
| 5,132,377 A | 7/1992 | Nakano et al. |
| 5,143,884 A | 9/1992 | Skoultchi et al. |
| 5,204,386 A | 4/1993 | Ersun-Hallsby et al. |
| 5,206,288 A | 4/1993 | Gosiewski et al. |
| 5,223,597 A | 6/1993 | Iwakiri et al. |
| 5,250,228 A | 10/1993 | Baigrie et al. |
| 5,286,821 A | 2/1994 | Skoultchi |
| 5,308,895 A | 5/1994 | Gan et al. |
| 5,310,835 A | 5/1994 | Skoultchi et al. |
| 5,344,890 A | 9/1994 | Miyazono et al. |
| 5,376,746 A | 12/1994 | Skoultchi |
| 5,401,805 A | 3/1995 | Chung et al. |
| 5,404,805 A | 4/1995 | Fujimoto et al. |
| 5,409,995 A | 4/1995 | Iwahara et al. |
| 5,411,998 A | 5/1995 | McArdle et al. |
| 5,420,223 A | 5/1995 | Johnson |
| RE35,058 E | 10/1995 | Yang |

(Continued)

FOREIGN PATENT DOCUMENTS

WO    WO 99/64475    12/1999

OTHER PUBLICATIONS

Kuhn et al., "Monoheteroarylborate", Zeitschrift fuer Naturforschung, B: Chemical Sciences 1997, 52(3), 351-354.*

(Continued)

Primary Examiner—Vasu Jagannathan
Assistant Examiner—Richard A Huhn
(74) Attorney, Agent, or Firm—Dobrusin & Thennisch PC

(57) ABSTRACT

The invention is amido-borate compounds containing one or more anionic amido-borate moieties comprising an organoborate anion wherein the boron atom is bonded to a nitrogen atom of ammonia or an organic compound containing one or more nitrogen atoms, such as a hydrocarbyl amine, a hydrocarbyl polyamine, or an aromatic heterocycle containing one or more nitrogen atoms, and a cationic counter ion.

11 Claims, No Drawings

U.S. PATENT DOCUMENTS

| | | |
|---|---|---|
| 5,506,326 A | 4/1996 | Kneafsey |
| 5,539,070 A | 7/1996 | Zharov et al. |
| 5,567,833 A | 10/1996 | Iwahara et al. |
| 5,599,856 A | 2/1997 | Gardner |
| 5,616,796 A | 4/1997 | Pocius et al. |
| 5,621,143 A | 4/1997 | Pocius |
| 5,674,941 A | 10/1997 | Cho et al. |
| 5,679,458 A | 10/1997 | Cho et al. |
| 5,681,910 A | 10/1997 | Pocius |
| 5,684,102 A | 11/1997 | Pocius |
| 5,686,544 A | 11/1997 | Pocius |
| 5,690,780 A | 11/1997 | Zharov et al. |
| 5,691,065 A | 11/1997 | Zharov et al. |
| 5,705,561 A | 1/1998 | Kozakiewicz et al. |
| 5,718,977 A | 2/1998 | Pocius |
| 5,721,281 A | 2/1998 | Blount |
| 5,795,657 A | 8/1998 | Pocius et al. |
| 5,807,910 A | 9/1998 | Tseng et al. |
| 5,817,376 A | 10/1998 | Everaerts et al. |
| 5,837,155 A | 11/1998 | Inagaki et al. |
| 5,859,155 A | 1/1999 | Furihata et al. |
| 5,872,197 A | 2/1999 | Deviny |
| 5,883,208 A | 3/1999 | Deviny |
| 5,912,433 A | 6/1999 | Pulido |
| 5,935,711 A | 8/1999 | Pocius et al. |
| 5,948,854 A | 9/1999 | De Buyl et al. |
| 5,952,409 A | 9/1999 | Boardman et al. |
| 5,990,036 A | 11/1999 | Deviny |
| 5,994,484 A | 11/1999 | Pocius |
| 6,001,928 A | 12/1999 | Harkness et al. |
| 6,008,284 A | 12/1999 | Nylund et al. |
| 6,008,308 A | 12/1999 | Pocius |
| 6,027,813 A | 2/2000 | Deviny |
| 6,054,548 A | 4/2000 | Currie et al. |
| 6,090,904 A | 7/2000 | Körner et al. |
| 6,093,778 A | 7/2000 | Pocius |
| 6,207,781 B1 | 3/2001 | Halloran et al. |
| 6,225,408 B1 | 5/2001 | Huang et al. |
| 6,252,023 B1 | 6/2001 | Moren |
| 6,339,114 B1 | 1/2002 | Klee et al. |
| 6,410,667 B1 | 6/2002 | Moren |
| 6,630,555 B2 | 10/2003 | Kendal et al. |
| 6,706,831 B2 | 3/2004 | Sonnenschein et al. |
| 6,710,145 B2 | 3/2004 | Sonnenschein et al. |
| 6,713,578 B2 | 3/2004 | Sonnenschein et al. |
| 6,713,579 B2 | 3/2004 | Sonnenschein et al. |
| 6,727,320 B2 | 4/2004 | Attarwala et al. |
| 6,730,759 B2 | 5/2004 | Sonnenschein et al. |
| 6,740,716 B2 | 5/2004 | Sonnenschein et al. |
| 6,762,260 B2 | 7/2004 | Sonnenschein et al. |
| 6,777,512 B1 | 8/2004 | Sonnenschein et al. |
| 6,806,330 B1 | 10/2004 | Sonnenschein et al. |
| 6,844,080 B2 | 1/2005 | Kneafsey et al. |
| 6,867,271 B1 | 3/2005 | Maandi et al. |
| 2002/0025381 A1* | 2/2002 | Sonnenschein et al. .. 427/372.2 |
| 2002/0028894 A1 | 3/2002 | Sonnenschein et al. |
| 2002/0032120 A1* | 3/2002 | Babb et al. .................. 502/102 |
| 2002/0111439 A1 | 8/2002 | Attarwala et al. |
| 2003/0018611 A1 | 1/2003 | Yano et al. |
| 2003/0109638 A1 | 6/2003 | Briggs et al. |
| 2003/0138651 A1 | 7/2003 | Kendall et al. |
| 2003/0226472 A1 | 12/2003 | Kneafsey et al. |
| 2004/0068067 A1 | 4/2004 | Kneafsey et al. |
| 2004/0082743 A1 | 4/2004 | Sonnenschein et al. |
| 2004/0242817 A1 | 12/2004 | Kendall et al. |
| 2005/0004332 A1 | 1/2005 | Jialanella et al. |
| 2005/0137370 A1 | 6/2005 | Jialanella et al. |

OTHER PUBLICATIONS

Chiou et al., "PyrazolyI[(methylthio)methyl]borates: hybrid ligands providing nitrogen and sulfur donors", Chem. Commun. 1999, 2, 159-160.*

Guidotti et al., J. Org. Chem. 2003, 68(14), 5445-5465.*

LaPointe et al., J. Am. Chem. Soc. 2000, 122(39), 9560-9561.*

E. Arancibia et al., Mechanism of Vinyl Monomer Polymerization in the Presence of Trialkylboranes and Inhibitors, Journal of Polymer Science: Part A-1, vol. 7 (1969), 3430-3433, Jun. 13, 1969, Universidad Técnica del Estado, Santiago, Chile.

F.S. Arimoto, Polymerization with Organoboron Compounds, Journal of Polymer Science: Part A-1, vol. 4, 275-282 (1966), E.I. DuPont de Nemours and Company, Inc., Wilmington, Delaware.

G.W. Bailey, Electron Microscope Studies on Polyethylene and Polypropylene, Journal of Polymer Science, vol. 62, (1962), pp. 241-249, Sep. 11, 1961, Baton Rouge, LA.

V.A. Dorokhov et al., Organoboron Compounds CCCIX. Complexes of Trialkylboranes with Amidines, ZH. Obshch. Khim., vol. 46, No. 55, 1057-1064, May 1976, Plenum Publishing Corporation, New York, NY.

V.A. Dodonov et al., Polymerization of Some Vinyl Monomers on Triisobutylboron-Containing Radical Initiators in the Presence of Hydroquinone and Benzoquinone, Polymer Science, vol. 35, No. 3, 1993, 403-406, Nizhnii Novgorod, 603600, Russia.

Seiichiro Fujisawa et al., Dental Self-Curing Resins. XI. Characterization of Several Complexes of Tri-N-Butyl Borane as an Initiator, 73:88532, XP002160417-Abstract & Iyo Kizai Kenkyusho Hokoku, Tokyo Ika Shika Daigaku (1969), 3, 64-71, Chemical Abstract.

J. Grotewold et al., Vinyl Monomer Polymerization Mechanism in the Presence of Trialkylboranes, Journal of Polymer Science: Part A-1, vol. 6, 3157-3162 (1968), Técnica del Estado, Santiago, Chile.

J. Harris et al., Proposed Mechanism for the Curing of Epoxy Resins with Amine-Lewis Acid Complexes or Salts, J. Appl. Polym. Sci., 10, 523-534 (1966), Koppers Co., Inc., Monroeville, PA.

Hoberg et al., Journal of Organometallic Chemistry, 1976, 118, C3-C5 (no translation provided), Elsevier Sequoia, S.A., Lausanne, Netherlands.

Herbert O. House, Modern Synthetic Reactions, 786 (1972), Georgia Institute of Technology, The Benjamin/Cummings Publishing Company.

Susumu Iwabuchi et al., The Copolymerization of Vinylhydroquinone and Acrylonitrile by Tri-N-Butylborane, Polymer Journal, vol. 6, No. 2, 185-190 (1974), Chiba 280, Japan.

Dr. Gordon M. Kline, Plastics Technical Section, Acceleration of Glycidyl Epoxy Resin-Anhydride Reactions, 149, 150, 152, 154, 155, 158, 160, 186, Apr. 1964, Sperry Gyroscope Co.

Roland Koester et al., Boron Compounds. XXVII. Borylation of Several Amino Carboxylic Acids, Justus Liebigs Ann, Chem. (1974), 112-119, XP000982170, (no translation provided).

V. Kokle et al., Journal of Polymer Science, The Molecular Structure of Polyethylene. XI. Weight- and Number-Average Molecular Weights of Selected Samples, vol. 62, 251-261 (1962), E.I. DuPont de Nemours and Co., Wilmington, Delaware.

Kuniharu Kojima et al., Polymer Letters, vol. 8, 541-547 (1970) Polymerization of Methyl Methacrylate by Trialklborane-Pyridine system, Chiba University, Yayoi-Cho, China.

Peter Love et al., Polar Substituent Effects in Gas-Phase Lewis Acid-Base Equilibria. I. Intrinsic Basicity of Amines, J. Amer. Chem. Soc. (May 8, 1968), 90(10), 2455-62, XP000982168, Tables 1, EX. T, Columns 4 and 5.

M. Tsukada et al., Grafting of Methyl Methacrylate Onto Silk Fibers Initiated by Tri-N-Butylborane, Journal of Applied Polymer Science, vol. 42, (1991), 2115-2121, John Wiley & Sons, Inc.

Martin Skoultchi et al., Chemical Abstract, vol. 119, 1983, 78, 119:74163c, Acrylic Adhesive Composition and Organoboron Initiator System, Ablestick Labs.

Yishihiro Kimura, Chemical Abstract, 128:218101s, Acrylic Adhesive Compositions, JP 10-046, 125, No. 18, 1998, 218099.

Chemical Abstract 116:195541w, Epoxy Resin Binder for Commutator Sheet Mica, Ivanilova et al.

Derwent Abstract 84-159009/26, DD207436-A, Veb Filmfab Wolfen, 1984.
Derwent Abstract 85-301176/48, SU 1155607, Kha Kirakosyan, 1985.
Derwent Abstract 87-331368/47, J62236-878-A, Sumitomo Elec Ind KK, 1987.
Derwent Abstract 88-202092/29, J63139-969-A, Kanegafuchi Chem KK, 1988.
Derwent Abstract 90-332394/44, J02240130-A, Denki Kagaku Kogyo KK, 1990.
Derwent Abstract 90-332395/44, J02240131-A, Denki Kagaku Kogyo KK, 1990.
Derwent Abstract 92-085634/11, J04029-391-A, Shinetsu Chem Ind KK, 1992.
Derwent Abstract 92-289585/35, JP04199694-A, Shinetsu Chem Ind Co. Ltd., 1992.
Derwent Abstract 94-164114/20, JP06107907-A, Nippon Zeon KK, 1994.
Derwent Abstract 95-041525/06, JP06322324-A, Shinetsu Chem Ind Co. Ltd., 1995.
Derwent Abstract 96-453820/45, ADGE=93.05.28, Adgeziv Co. Ltd., RU2054022-C1, 1996.
Derwent Abstract 95-049086/07, JP06330015-A, Nissan Motor Co. Ltd., 1995.
Derwent Abstract 96-484098, SU 1457392A1, Dodonov et al, 1996.
Derwent Abstract 97-010377, SU 1609117A1, Dodonov et al, 1997.
Derwent Abstract 97-064052, SU162491A1, Dodonov et al, 1997.
Derwent Abstract 97-529863/49, JP09208921-A, Shinetsu Chem Ind Co. Ltd., 1997.
Derwent Abstract 98-189554/17, JP10046126-A, Nippon Synthetic Chem Ind Co., 1998.
Derwent Abstract 98-343543/30, JP101360612-A, Nippon Synthetic Chem Ind Co., 1998.
Derwent Abstract 98-357757/31, JP10140119-A, Nippon Synthetic Chem Inc. Co., 1998.
Derwent Abstract 99-010842/02, DE19738208-A1, T. Tseng et al, 1999.
Derwent Abstract 99-283642/24, JP11092593-A, Hitachi Chem Co. Ltd., 1999.
U.S. Appl. No. 60/724,943, filed Oct. 7, 2005, Shaoguang et al. Amido-Organoborate Initiator Systems.
Accelerated Organoborane Initiated Polymerizable Compositions, Gary L. Jialanella et al., filed Oct. 12, 2006, U.S. Appl. No. 11/546,794.

* cited by examiner

AMIDO-ORGANOBORATE INITIATOR SYSTEMS

This application claims priority from U.S. Provisional Application 60/724,943 filed Oct. 7, 2005.

FIELD OF THE INVENTION

This invention relates to amido-organoborates initiator systems which are useful for polymerizable compositions containing such systems.

BACKGROUND OF THE INVENTION

Organoborane based systems are known to initiate free radical polymerization and promote adhesion to low surface energy substrates due to their ability to generate radicals to polymerize compounds capable of free radical polymerization such as compounds containing unsaturated moieties. The oxidation of organoborane based systems with molecular oxygen forms energetic peroxides which are exothermic and can be pyrophoric if not carefully controlled. Due to the high reactivity of organoboranes with oxygen, systems have been developed which block the organoborane center to stabilize the organoborane and which unblock the organoborane center to initiate free radical formation. The role of the blocking group is to render the organoborane center less susceptible to oxygen insertion and radical initiation.

EP 1,201,722 discloses the use of L-selectride and phenyl borate as the borane precursors with hydride and phenyl anions as the blocking groups. A series of patents issued to Skoultchi, U.S. Pat. Nos. 5,106,928; 5,143,884; 5,286,821; 5,310,835 and 5,376,746 (all incorporated herein by reference) and to Zharov, et al., U.S. Pat. Nos. 5,539,070; 5,690,780; and 5,691,065 (all incorporated herein by reference) disclose polymerizable acrylic compositions which are particularly useful as adhesives wherein organoboron amine complexes are used to initiate cure. Pocius in a series of patents, U.S. Pat. Nos. 5,616,796; 5,621,143; 5,681,910; 5,686,544; 5,718,977; and 5,795,657 (all incorporated herein by reference) disclose amine organoboron complexes using a variety of amines to complex the organoboron, such as polyoxyalkylene polyamines and polyamines which are the reaction product of diprimary amines and compound having at least two groups which react with a primary amine. A series of patents by Sonnenschein et al. U.S. Pat. Nos. 6,806,330; 6,730,759; 6,706,831; 6,713,578; 6,713,579 and 6,710,145, disclose amine organoboron complexes wherein the organoboron is a trialkyl borane and the amine is selected from the group of amines having an amidine structural component; aliphatic heterocycles having at least one nitrogen in the heterocyclic ring; an alicyclic compound having bound to the ring a substituent having an amine moiety; primary amines which in addition have one or more hydrogen bond accepting groups wherein there are at least two carbon atoms between the primary amine and the hydrogen bond accepting group; and conjugated imines. These patents disclose polymerizable compositions containing the amine organoboron complexes, one or more of monomers, oligomers or polymers having olefinic unsaturation which are capable of polymerization by free radical polymerization and that the polymerizable compositions can be used as adhesive, sealant, coating or ink compositions. Kendall et al., U.S. Pat. No. 6,630,555 (incorporated herein by reference) discloses useful boron containing compounds for initiating polymerization are internally blocked organoborates, incorporated herein by reference. The term "internally blocked" in reference to the organoborates is described as a four coordinate boron atom being part of an internal ring structure bridged across two of the four boron coordinates or valences. Kneafsey et al., U.S. Publication Number 2003/0226472 and Kneafsey et al., U.S. Publication Number 2004/0068067 disclose another class of organoborates useful in initiating polymerization is tetrahydrocarbyl borates (also known as quaternary boron salts), both incorporated herein by reference.

Low surface energy olefins such as polyethylene, polypropylene and polytetrafluroethylene have a variety of attractive properties in a variety of uses, such as toys, automobile parts, furniture applications and the like. Because of the low surface energy of these plastic materials, it is very difficult to find adhesive compositions that bond to these materials. The commercially available adhesives that are used for these plastics require time consuming or extensive pretreatment of the surface before the adhesive will bond to the surface. Such pretreatments include corona treatment, flame treatment, the application of primers, and the like. The requirement for extensive pretreatment of the surface results in significant limitations to the designers of automobile components, toys, furniture and the like.

There is a continued need for free radical polymerization initiator systems that are stable under storage conditions, which initiate rapid cure once polymerization is initiated and which are useful in polymerizable systems which are capable of bonding to low surface energy substrates.

SUMMARY OF INVENTION

In one embodiment, the invention is:
a) amido-borate compounds containing one or more anionic amido-borate moieties comprising an organoborate wherein the boron atom is bonded to at least one nitrogen atom of ammonia, or an organic compound containing a nitrogen atom, such as a hydrocarbyl amine, a hydrocarbyl polyamine, or an aromatic heterocycle containing one or more nitrogen atoms and optionally one or more heteroatoms or heteroatom containing functional moieties, and one or more cationic counter ions.

In another embodiment the amido-borate is a compound comprising one or more tetravalent boron anions and one or more of:
i) an organic compound containing a nitrogen atom and a cation or
ii) an ammonium cation;

wherein the each of the one or more tetravalent boron atoms is bonded to the nitrogen atom of an ammonium cation or an organic compound containing a nitrogen atom.

In another embodiment the amido-borate is a compound comprising at least one tetravalent boron anion wherein the boron anion is bonded to the nitrogen atom an organic compound which contains a nitrogen atom and one or more cations and the number of borate anions and cations is the same.

In another embodiment the amido-borate is a compound comprising one or more tetravalent boron anions bonded to an ammonium cation.

In another embodiment the amido-borates comprises two or more amido-borates each comprising a tetravalent boron anion wherein at least one of the borate anions is bonded to the nitrogen atom of an organic compound; and at least one of the borate anions is bonded to the nitrogen of an ammonium cation; and one or more additional cations wherein the number of additional cations is the same as the number of tetravalent boron atoms bonded to the nitrogen atom of an organic compounds containing at least one nitrogen atom.

The amido-borates are useful in two part polymerizable compositions comprising in one part, one or more amido-borate compounds and in the second part, a liberating compound which reacts with the nitrogen atoms bound to the boron atom upon contact with the amido-borate to form an organoborane radical and one or more compounds capable of free radical polymerization.

The amido-borates enable polymerizable compositions which are stable at, or near, ambient temperature and can be cured upon demand by contacting the two parts of the composition. Furthermore, the polymerizable compositions containing the amido-borates can form good bonds to low surface energy substrates without the need for primers or surface treatment. Polymerized compositions based on the amido-borates demonstrate excellent cohesive and adhesive strength at elevated temperatures and thus demonstrate excellent stability at high temperatures.

DETAILED DESCRIPTION OF THE INVENTION

The amido-borates comprise one or more amido-borate anions and one or more corresponding cations which neutralize the amido-borate anion. A borate is a salt of a positive cation and an anionic tetravalent boron. The amido-borates are organoborates wherein one of the ligands on the boron atom is the nitrogen of ammonia or an organic compound which contains a nitrogen atom and which may contain a heteroatom or a heteroatom containing functional moieties wherein the nitrogen may be quaternary and cationic. In some embodiments, the cation can be the nitrogen bonded to the boron in the form of a quaternary nitrogen. This is especially true where the nitrogen compound used to form the amido-borate has more than one nitrogen which is bonded to more than one boron atoms of organoboranes to form the amido-borate. The organoborane bonded to the nitrogen atom to form the amido-borate comprises a boron atom with three bonds to hydrocarbyl moieties wherein the hydrocarbyl moieties may further comprise one or more heteroatoms or heteroatom containing functional groups which do not interfere in the described function of the amido-borate compounds described herein. Preferred heteroatoms which may be present in hydrocarbyl moieties as described herein include oxygen, sulfur, nitrogen, silicon, halogens, and the like with oxygen being most preferred. Preferred heteroatom containing functional groups which may be present as part of hydrocarbyl moieties as described herein include ethers, thioethers, amines, silanes, siloxanes and the like with ethers being most preferred. The boron atom may be bonded to three separate hydrocarbyl moieties or may be bonded to two hydrocarbyl moieties wherein one hydrocarbyl moiety has two bonds to the boron atom thereby forming one or more cyclic ring(s). The organoborane used to prepare the amido-borate is preferably a trialkyl borane or an alkyl cycloalkyl borane. Preferably, such organoborane corresponds to the formula:

$$B\text{-}(R^1)_3$$

wherein B represents boron; and $R^1$ is separately in each occurrence hydrogen, an alkyl or cycloalkyl group, or two or more of $R^1$ may combine to form a cycloaliphatic ring; preferably $R^1$ is a $C_{1-10}$ alkyl, $C_{3-10}$ cycloalkyl, or two or more of $R^1$ may combine to form a cycloaliphatic ring; with the proviso that only 1 or 2 of $R^1$ may be hydrogen. More preferably, none of $R^1$ is hydrogen. More preferably, $R^1$ is $C_{1-4}$ alkyl, and most preferably $C_{2-4}$ alkyl. Among preferred organoboranes are tri-ethyl borane, tri-isopropyl borane and tri-n-butylborane.

The nitrogen containing portion of the amido-borate may be derived from ammonia or any organic compound containing a nitrogen atom which is capable of bonding to boron and is preferably derived from ammonia, a hydrocarbyl amine or a polyamine. The nitrogen atoms of such compounds bonded to the boron atoms to form the borates can be primary, secondary, or quaternary, preferably secondary or tertiary or quaternary. In another preferred embodiment the nitrogen atom bonded to the organoborane to prepare the amido-borate is a nitrogen located in or on the ring of a heteroaromatic cyclic compound. In those embodiments where the nitrogen is quaternary, the quaternary nitrogen portion of the amido-borate is the cationic counterion for the borate anion portion of the compound to which the quaternary nitrogen atom is bonded. The hydrocarbyl amine or polyamine and the nitrogen containing aromatic heterocylic compound may contain heteroatoms as described hereinbefore or be further substituted with substituents which do not interfere with the functioning of such compounds in the compositions of the invention as described hereinbefore. The hydrocarbyl amines preferably correspond to the formula $$H_{2-r}\text{---}N\text{---}(R^2)_r$$

wherein $R^2$ is independently in each occurrence an alkyl, cycloalkyl, aryl, alkaryl, or aralkyl group; wherein such group may optionally contain one or more heteroatoms, one or more heteroatom containing functional groups, as described hereinbefore or protons. $R^2$ is preferably $C_{1-10}$ alkyl, $C_{3-10}$ cycloalkyl, $C_{6-12}$ aryl, $C_{7-20}$ alkaryl or $C_{7-20}$ aralkyl; wherein such group may optionally contain one or more heteroatoms of O or S, preferably O, or O or S containing heteroatom functional moieties. $R^2$ is more preferably $C_{1-4}$ alkyl or $C_{1-10}$ alkoxyalkyl; even more preferably methyl, ethyl, propyl, methoxypropyl, ethoxypropyl or proproxypropyl. In reference to alkoxyalkyl, the number of carbon atoms refer to the total carbon atoms in the moiety. The hydrocarbyl polyamines preferably correspond to the formula

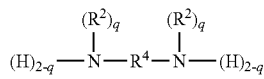

wherein $R^2$ is as described hereinbefore;

$R^4$ is independently in each occurrence a divalent hydrocarbyl moiety which may contain one or more heteroatoms or one or more heteroatom containing functional moieties as described hereinbefore;

r is independently in each occurrence 0, 1 or 2; and q is independently in each occurrence 1 or 2.

The aromatic nitrogen containing heterocyclic compounds preferably correspond to the formula

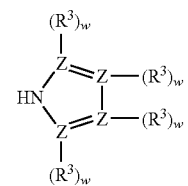

wherein $R^3$ is independently in each occurrence hydrogen, an alkyl, an alkoxyl, aralkyl or an aryl group; wherein such group may optionally contain one or more heteroatoms, one or more heteroatom containing functional moieties, as described hereinbefore, or protons; Z is independently in each occurrence N, Si, P or C and w is 0 or 1 with the proviso that where Z is N or P, w can only be 0, whereas when Z is C or Si; w can only be 1. Preferably Z is N or C. $R^3$ is preferably hydrogen, $C_{1-10}$ alkyl, $C_{3-10}$ cycloalkyl, $C_{6-12}$ aryl, $C_{7-20}$ alkaryl or $C_{7-20}$ aralkyl; wherein such group may optionally contain one or more heteroatoms of O or S, preferably O, or one or more O or S heteroatom containing functional moieties. $R^3$ is more preferably hydrogen, $C_{1-4}$ alkyl or a $C_{1-10}$ alkoxyalkyl even more preferably hydrogen, methyl, ethyl, propyl and most preferably hydrogen. Preferably $R^4$ is independently in each occurrence $C_{2-20}$ alkylene, $C_{3-20}$ cycloalkylene, $C_{6-20}$ arylene, $C_{7-20}$ alkarylene or $C_{7-20}$ aralkylene; more optionally containing one or more heteroatoms or heteroatom containing functional moieties; more preferably $C_{2-20}$ alkylene or $C_{2-20}$ alkylene groups containing one or more oxygen atoms and even more preferably $C_{2-4}$ alkylene. Preferred heteroatoms are O or S, with O most preferred.

The cation which forms the salt with the amido-borate can be any cation which forms a salt with the amido-borate. The cation can be any group IA and group IIA metal, any inorganic cation or organic cation. Preferably, the cation is an onium ion or an alkali metal ion. More preferably the cation is sodium, potassium, a phosphonium or an ammonium ion. Preferred ammonium ions are tetraalkyl ammonium ions, with tetramethyl ammonium ion being most preferred. Preferred phosphonium ions are tetraalkyl phosphonium or tetraaryl phosphonium; with tetrabutyl phosphonium and tetraphenyl phosphonium preferred.

The amido-borates preferably correspond to one of the formulas

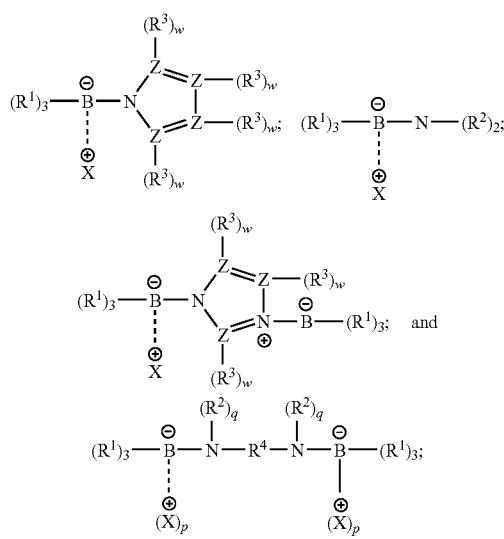

wherein $R^1$, $R^2$, $R^3$, $R^4$ and w are as described hereinbefore;

X is independently in each occurrence a cation;

p is independently in each occurrence 0 or 1;

q is independently in each occurrence 1 or 2 wherein q is 2, the nitrogen atom is the cation counter-balancing the borate anion;

with the proviso that the sum of p and q on each linked boron and nitrogen pair is 2; and the sum of the p is 1 or 2. Where q is 2, the nitrogen to which it is bonded is quaternary and carries a positive charge which balances the negative charge found on the boron of the borate and a cation is not needed to neutralize the borate.

Preferably, X is independently in each occurrence an onium or an alkali metal ion; more preferably X is an ammonium, phosphonium, potassium or sodium cation, even more preferably X is a tetraalkyl ammonium, tetraalkyl phosphonium, tetraaryl phosphonium or sodium and most preferably X is tetramethyl ammonium, tetrabutyl ammonium, tetrabutyl phosphonium tetraphenyl phosphonium.

In another embodiment the cationic species can have more than one cationic species that form salts with the borate anions. Thus, the cationic species can form a salt with more than one borate species. Preferably, the cationic species with more than one cation have 2 to 4, preferably 2 or 3 cations and even more preferably 2. Among preferred cationic species having more than one cation are compounds having 2 or more ammonium or phosphonium cations, with compounds having two ammonium cations being preferred. Examples of such compounds include 1,2(di(trimethylammonium)) ethane. In the embodiment where the cationic species have more than one cation, the amido-borates preferably correspond to the formulas:

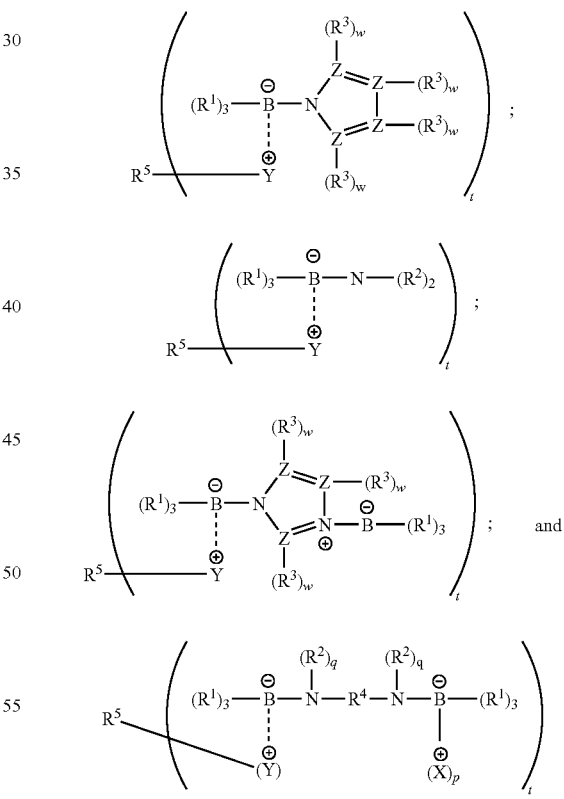

wherein $R^1$, $R^2$, $R^3$, $R^4$, w, X, p and q are as described hereinbefore;

$R^5$ is independently in each occurrence a t-valent hydrocarbyl group optionally containing one or more heteroatoms or heteroatom containing functional moieties, as described hereinbefore;

Y is independently in each occurrence

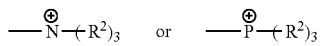

and t is independently in each occurrence 2 or greater. Preferably, t is 2 or 4, even more preferably 2 or 3 and most preferably 2. More preferably $R^5$ is independently in each occurrence a t-valent $C_{2-20}$ alkylene, $C_{3-20}$ cycloalkylene, $C_{6-20}$ arylene, $C_{7-20}$ alkarylene, or $C_{7-20}$ aralkylene optionally containing one or more heteroatoms or heteteroatom containing functional moieties, preferred heteroatoms are sulfur and oxygen with oxygen most preferred; and More preferably $R^5$ is a t-valent alkylene group, and more preferably a t-valent $C_{2-6}$ alkylene group. Most preferably $R^5$ is a divalent $C_{2-4}$ alkylene group.

The amido-borates are used in the polymerizable compositions of the invention in an amount sufficient to initiate polymerization when the amine is liberated and to facilitate bonding of the polymerizable compositions where desired. Preferably, the amido-borate is present in polymerizable compositions in an amount of about 0.1 part by weight based on 100 parts by weight of the composition or greater, more preferably about 0.5 parts by weight or greater and most preferably about 1 part by weight or greater. Preferably, the amido-borate is present in polymerizable compositions in an amount of about 30 parts by weight or less based on 100 parts by weight of the composition, more preferably about 20 parts by weight or less and most preferably about 10 parts by weight or less.

The amido-borates can be prepared from the base amines described above, such amines are commercially available. The amine can be contacted with a base, in a solvent and no solvent if the amine is liquid, resulting in a salt. Inert organic solvents such as tetrahydrofuran may be used. A salt of the amine and the cation from the base is formed. The resulting salt is contacted with a trivalent organoborane to form the amido-borate. The contacting is preferably performed in a vacuum or under an inert atmosphere. Preferably, the process is performed at ambient temperatures. If a solvent is used, it can be removed in vacuo.

The amido-borate is capable of forming a trivalent organoboron compound. The amido-borates are tetravalent in that they have four bonds to the boron. The free radical generating species, the trivalent boron compound, is formed when the amido-borate is contacted with a liberating compound. The trivalent borane generates free radicals by reacting with environmental oxygen. The trivalent organoborane is readily attacked by oxygen to form radicals which initiate free radical polymerization in contact with compounds which polymerize in the presence of free radicals. Contacting the amido-borate with the liberating compound causes the abstraction of one of the ligands bonded to the boron atom to convert it to a trivalent borane. The liberating agent can be any compound which reacts with the nitrogen atom of the amido-borate. Generally the liberating agent has a greater affinity for the nitrogen of the amido-borate than the boron atom has for the nitrogen atom. The liberation of the amine or ammonium from the amido-borate can occur with any chemical for which the exchange energy is favorable, such as mineral acids, organic acids, Lewis acids, isocyanates, acid chlorides, sulphonyl chlorides, aldehydes, and the like. Preferred liberating compounds are acids and isocyanates. In those embodiments where a compound having a heterocylic compound capable of ring opening polymerization is present and the initiator for the ring opening polymerization is a Lewis acid, the liberating compound may be omitted as Lewis acids may also function as the liberating compound. If the Lewis acid is used as the liberating compound and heterocyclic ring opening polymerization initiator, no additional amounts are needed over those amounts needed to initiate polymerization. The compositions of the invention will comprise a sufficient amount of liberating compound to initiate polymerization at an acceptable rate. Preferably, the liberating compound is present in a molar equivalent basis, or greater, as compared to the amido-borate. Preferably, the liberating compound is present in an amount of about 0.5 molar equivalents or greater based on the molar equivalents of the organoborane, more preferably in an amount of about 1.0 molar equivalents or greater and most preferably about 1.5 molar equivalents or greater. Preferably, the liberating compound is present in an amount of about 100 molar equivalents or less based on the molar equivalents of the organoborane, more preferably in an amount of about 50 molar equivalents or less and most preferably about 25 molar equivalents or less.

Preferably, the polymerizable compositions based on the amido-borates further comprise a second amine which may further comprise polar functional groups. The second amine can be any amine which stabilizes the compositions of the invention against undesired polymerization. Preferred polar functional groups are ether groups, thioether groups, secondary and tertiary amines and the like. Preferably, the second amine comprises an alkoxy alkyl amine or a polyamine, that is, a compound having two or more amino groups. The alkyl backbone of the second amine is preferably $C_{2-8}$ alkyl group and most preferably $C_{2-4}$ alkyl. Preferably, the alkyl group on the alkoxy group is a $C_{1-8}$ alkyl, more preferably a $C_{1-4}$ alkyl and most preferably a methyl group. Preferred alkoxy alkyl amines include methoxypropyl amine, methoxyethylamine and ethoxypropylamine; with methoxypropyl amine most preferred. The second amine is present in a sufficient amount to stabilize the compositions of the invention to prevent premature polymerization. Preferably, the second amine is present in an amount about 1 mole percent or greater based on the moles of the amido-borate present and more preferably an amount of about 10 mole percent or greater. Preferably, the second amine is present in an amount of about 1,000 mole percent or less based on the moles of the amido-borate present or less and more preferably of about 300 mole percent or less.

Compounds capable of free radical polymerization which may be used in the polymerizable compositions include any monomers, oligomers, polymers or mixtures thereof which contain olefinic unsaturation which can polymerize by free radical polymerization. Such compounds are well known to those skilled in the art. Mottus, U.S. Pat. No. 3,275,611, provides a description of such compounds at column 2, line 46 to column 4, line 16, incorporated herein by reference. Preferred classes of compounds containing olefinic unsaturation are disclosed in Sonnenschein et al., U.S. Pat. No. 6,730,759 (column 9, line 7 to line 54); U.S. Pat. Nos. 6,706,831; 6,713,578; 6,713,579 and 6,710,145 relevant portions incorporated herein by reference. Examples of preferable acrylates and methacrylates are disclosed in Skoultchi, U.S. Pat. No. 5,286,821 at column 3, lines 50 to column 6, line 12, incorporated herein by reference and Pocius, U.S. Pat. No. 5,681,910 at column 9, line 28 to column 12, line 25, incorporated herein by reference. Also useful in these compositions are acrylate crosslinking molecules including ethylene glycol dimethacrylate, ethylene glycol diacrylate, triethyleneglycol dimethacrylate, diethylene glycol bismethacryloxy carbonate, polyethylene glycol diacrylate, tetraethylene glycol dimethacrylate, diglycerol diacrylate, diethylene glycol dimethacrylate, pentaerythritol triacrylate, trimethylolpropane trimethacrylate, isobomylmethacrylate and tetrahydrofurfuryl methacrylate. In the embodiment where the composition is used as an adhesive, acrylate and/or methacrylate based compounds are preferably used as the compounds capable of free radical polymerization. The most preferred acrylate and methacrylate compounds include methylmethacrylate, butylmethacrylate, 2-ethylhexylmethacrylate, cyclohexylmethylmethacrylate and (tetrahydrofurfuryl) methacrylate. Preferred amounts of compounds capable of free radical polymerization are about 10 parts by weight or greater based on 100 parts of the total formulation weight, more preferably about 20 parts by weight or greater and most preferably about 30 parts by weight or greater. Preferred amounts of compounds capable of free radical polymerization are preferably about 90 parts by weight or less based on 100 parts of the total formulation weight, more preferably about 85 parts by weight or less and most preferred 80 parts by weight or less.

In another embodiment, the invention of the polymerizable compositions may further comprise one or more compounds, oligomers or prepolymers having a siloxane backbone and reactive moieties capable of polymerization, a catalyst for the polymerization of the one or more compounds, oligomers or prepolymers having a siloxane backbone and reactive moieties capable of polymerization as disclosed in U.S. Pat. No. 6,777,512, titled AMINE ORGANOBORANE COMPLEX INITIATED POLYMERIZABLE COMPOSITIONS CONTAINING SILOXANE POLYMERIZABLE COMPONENTS (column 12, line 66 to column 15, line 54), incorporated herein by reference.

The polymerizable compositions of the invention may further contain a stabilizing amount of a dihydrocarbyl hydroxyl amine or stable nitroxy radicals such as those disclosed in Jialanella, U.S. Patent Publication 2005/0004332, incorporated herein by reference. Stabilizing as used herein refers to preventing polymerization until desired. Generally this means that polymerization is inhibited under normal storage conditions. Normal storage conditions mean storage at a temperature of about 0° C. to about 40° C., wherein the adhesive is stored in a sealed container. A stable composition is one that does not experience undesired viscosity growth during a defined period. Viscosity growth is evidence of polymerization of the monomers present. In a preferred embodiment, a composition is stable if the viscosity does not increase more than 150 percent over a time period of 30 days when stored at temperatures of 40° C. or less, more preferably 100 percent or less over a time period of 30 days and most preferably 50 percent or less over a time period of 30 days. Preferred dihydrocarbyl hydroxyl amines useful herein include any such compounds which, when included in the compositions of this invention, improve the stability of the compositions as described herein. Among preferred dihydrocarbyl hydroxyl amines are hydroxylamine freebase from BASF, hydroxylamine derivatives from Mitsui Chemicals America, Inc. and Irgastab™ FS Products from Ciba Specialty Chemicals which contains oxidized bis(hydrogenate tallow alkyl) amine, also described as bis(N-dodecyl) N-hydroxyl amine. The dihydrocarbyl hydroxyl amines are utilized in sufficient amounts to stabilize the compositions of the invention. Preferably, the dihydrocarbyl hydroxyl amines are used in an amount of about 1 part per million by weight of the compositions of the invention or greater, more preferably about 2 parts per million or greater and most preferably about 5 parts per million or greater. Preferably, the dihydrocarbyl hydroxyl amines are used in an amount of about 100,000 parts per million by weight of the compositions of the invention or less, more preferably about 50,000 parts per million or less, even more preferably about 25,000 parts per million or less and most preferably about 10,000 parts per million or less.

The compositions of the invention may further comprise an accelerator for the cure of the polymerizable compositions. The accelerators comprise at least one compound containing a quinone structure or at least one compound containing at least one aromatic ring and one or more, preferably two, substituents on the aromatic ring selected from hydroxyl, ether and both. When a compound is used, the substituents are located either ortho or para with respect to one another. In one embodiment, the accelerator is any compound containing a quinone structure which compound accelerates the cure of the polymerizable compositions, as described in Jialanella, U.S. Patent Publication 2005-0004332, incorporated herein by reference. For adhesive compositions preferred quinones also facilitate adhesion of the polymerizable compositions to substrate surfaces. More preferred quinones include anthraquinone, benzoquinone, 2-phenylbenzoquinone, orthoquinone and substituted benzoquinone. Most preferred quinone containing compounds include benzoquinone. The amount of quinone used is that amount which accelerates cure of the compositions and does not inhibit adhesion of the composition to the substrate surface. If too little is used, there is no significant increase in cure speed. If too much is used, the composition will not adhere to a substrate surface. Preferably, the quinone is used in an amount of about 0.01 part by weight based on 100 parts of the polymerizable composition or greater, more preferably about 0.02 parts by weight or greater, and most preferably about 0.04 parts by weight or greater. Preferably, the quinone is used in an amount of about 0.1 part by weight based on 100 parts of the polymerizable composition or less, more preferably about 0.8 parts by weight or less, and most preferably about 0.4 parts by weight or less.

In another embodiment, the accelerator comprises at least one compound containing at least one aromatic ring and at least one, preferably two, substituents on the aromatic ring selected from hydroxyl, ether and both, wherein the two substituents are located either ortho or para with respect to one another. The substituted aromatic ring containing compounds is used in conjunction with a compound having a peroxy moiety as described in Jialanella, U.S. Patent Publication Number 2005-0004332, incorporated herein by reference. The substituted aromatic compound can contain any aromatic moiety, including those with multiple ring structures. The substituted aromatic compounds preferably contain two or more functional groups selected from hydroxy and ether. Preferably, the substituted aromatic compounds contain at least one hydroxy and another hydroxy or ether moiety. Most preferably, the substituted aromatic compound contains at least one hydroxy and at least one ether moiety. Preferably, the substituted aromatic compounds contain benzene, anthracene or naphthalene aromatic ring structures. The substituted aromatic compounds may be substituted with any substituent which does not interfere with the formation of free radicals or the reaction of the free radicals with other compounds. Preferred substituents include alkyl, aryl, or aralkyl groups, and oxygen or sulfur heteroatoms containing groups. Most preferred substituents include aryl groups and heteroatom containing groups. Among most preferred substituted aromatic ring containing compounds are anthrahydroquinones, naphthahydroquinones, methyl ether of hydroquinone and alkylethers of hydroquinone. The amount of substituted aromatic ring containing compound used is that amount which accelerates cure of the compositions, and which does not inhibit adhesion of the composition to the substrate surface used. If too little is used, there is no significant increase in cure speed. If too much is used, the composition will not adhere to a substrate surface. Preferably, the substituted aromatic ring containing compound is used in an amount of about 0.1 part by weight or greater of the polymerizable composition based on 100 parts, more preferably about 1 part by weight or greater, and most preferably about 2 parts by weight or greater. Preferably, the substituted aromatic ring-containing compound is used in an amount of about 4 parts by weight or less of the polymerizable composition based on 100 parts, more preferably about 3 parts by weight or less, and most preferably about 2.5 parts by weight or less.

In conjunction with the substituted aromatic ring-containing compound a peroxy-containing compound is used. Any peroxy-containing compound that reacts with the substituted aromatic ring-containing compound to form free radicals may be used. Preferred peroxy-containing compounds include dialkyl peroxides, diaryl peroxides, diacyl peroxides, alkyl hydroperoxides, aryl hydroperoxides, and aryl hydroperoxides. More preferred peroxy-containing compounds include t-butyl peroxides, benzoyl peroxide, t-butyl perbenzoate. Most preferred peroxy-containing compounds include benzoyl peroxide and t-butyl perbenzoate. The amount of peroxy-containing containing compound used is that amount which accelerates cure of the compositions. If too little is used, there is no significant increase in cure speed. If too much is used, the adhesive does not bond to polyolefins. Preferably, the peroxy-containing compound is used in an amount of about 0.1 part by weight or greater of the polymerizable composition based on 100 parts, more preferably about 1 part by weight or greater, and most about 2 parts by weight or greater. Preferably, the peroxy-containing compound is used in an amount of about 4 parts by weight or less of the polymerizable composition based on 100 parts, more preferably about 3 parts by weight or less, and most preferably about 2.5 parts by weight or less. Preferably, the relative amount of peroxy containing compound to substituted aromatic ring containing compound is selected such that the majority of the resultant free radicals generated by the peroxy compound reacts with the substituted aromatic ring compound. Thus, a molar ratio of peroxy containing compound to aromatic ring containing compound is one or less. If the ratio is too high, then no adhesion to polyolefins would be observed. If the ratio is too low, then the adhesive cure rate is not increased. Preferably, the molar ratio of peroxy containing compound to substituted aromatic ring containing compound is about 1:4 or greater, and most preferably about 2:3 or greater. Preferably, the molar ratio of peroxy containing compound to substituted aromatic ring containing compound is about 1:1 or less.

Preferably, the accelerator is located in the part that does not contain the amido-borate. Often the part containing the amido-borate is referred to as the hardener side, and the other part is referred to as the resin side because the largest part of the polymerizable compound is found in this part.

Hydrocarbyl as used herein means any moiety having both carbon and hydrogen atoms and includes saturated and unsaturated, branched and unbranched, hydrocarbon chains and aromatic and non-aromatic ring structures. Alkyl refers to branched and unbranched saturated hydrocarbon chains. Alkenyl refers to branched and unbranched unsaturated hydrocarbon chains. Aryl means an aromatic hydrocarbon moiety. Alkaryl means an aromatic hydrocarbon moiety with a straight or branched hydrocarbon chain attached. Aralkyl means a straight or branched hydrocarbon chain with an aryl group attached. Acyl means a hydrocarbyl and carbonyl moiety. Alkylene means a divalent alkyl moiety. Unless otherwise stated these moieties may be substituted with any other substituent which does not significantly interfere in the function of the compound to which the moiety is attached or bonded.

The two-part polymerizable compositions or adhesive compositions of the invention are suited for use with conventional, commercially available dispensing equipment for two-part compositions. Once the two-parts have been combined, the composition should be used quickly, as the useful pot life (open time) may be short depending upon the monomer mix, the amount of amido-borate, the amount of catalyst and the temperature at which the bonding is performed. The adhesive compositions of the invention are applied to one or both substrates and then the substrates are joined together, preferably with pressure to force excess composition out of the bond line. In general, the substrates should be contacted with the composition disposed therebetween shortly after the composition has been applied, preferably within about 10 minutes. The typical bond line thickness is about 0.005 inches (0.13 mm) to about 0.03 inches (0.76 mm). The bond line can be thicker if a gap filling is needed as the composition of the invention can function as both an adhesive and a gap filler. The bonding process can easily be carried out at room temperature, and to improve the degree of bonding, it is preferable to keep the temperature below about 55° C. and more preferably below about 40° C.

The compositions may further comprise a variety of optional additives. One particularly useful additive is a thickener such as medium to high (about 10,000 to about 1,000,000) molecular weight polymethyl methacrylate which may be incorporated in an amount of about 10 to about 60 weight parts, based on 100 parts of the composition. Thickeners may be employed to increase the viscosity of the composition to facilitate application of the composition.

Another particularly useful additive is an elastomeric material. The materials may improve the fracture toughness of compositions made therewith which can be beneficial when, for example, bonding stiff, high yield strength materials such as metal substrates that do not mechanically absorb energy as easily as other materials, such as flexible polymeric substrates. Such additives can be incorporated in an amount of about 5 parts to about 35 parts by weight, based on 100 parts of the composition. Useful elastomeric modifiers include chlorinated or chlorosulphonated polyethylenes such as Hypalon™ 30 (commercially available from E. I. Dupont de Nemours & Co., Wilmington, Del.) and block copolymers of styrene and conjugated dienes (commercially available from Dexco Polymers under the Trademark Vector, and Firestone under the Trademark Stereon). Also useful, and even more preferred, are certain graft copolymer resins such as particles that comprise rubber or rubber-like cores or networks that are surrounded by relatively hard shells, these materials often being referred to as "core-shell" polymers. Most preferred are the acrylonitrile-butadiene-styrene graft copolymers available from Rohm and Haas. In addition to improving the fracture toughness of the composition, core-shell polymers can also impart enhanced spreading and flow properties to the uncured composition. These enhanced properties may be manifested by a reduced tendency for the composition to leave an undesirable "string" upon dispensing from a syringe-type applicator, or sag or slump after having been applied to a vertical surface. Use of more than about 20 parts of a core-shell polymer additive is desirable for achieving improved sag-slump resistance. Generally, the amount of toughening polymer used is that amount which gives the desired toughness to the polymer or the adhesive prepared.

The polymerizable compositions utilizing amido-borates of the invention may be used in a wide variety of ways, including as adhesives, coatings, primers, to modify the surface of polymers, and injection molding resins. They may also be used as matrix resins in conjunction with glass and metal fiber mats such as in resin transfer molding operations. They may further be used as encapsulants and potting compounds such as in the manufacture of electrical components, printed circuit boards and the like. Quite desirably, they provide polymerizable adhesive compositions that can bond a wide range of substrates, including polymers, wood, ceramics, concrete, glass and primed or unprimed metals. Another desirable related application is their use in promoting adhesion of paints to low surface energy substrates such as polyethylene, polypropylene, polyethyleneterephthalate, polyamides, and polytetrafluoroethylene, and their co-polymers. In this embodiment, the composition is coated onto the surface of the substrate to modify the surface to enhance the adhesion of the final coating to the surface of the substrate. Thereafter the coating can be applied to the treated surface.

Polymerizable compositions are especially useful for adhesively bonding low surface energy plastic or polymeric substrates that historically have been very difficult to bond without using complicated surface preparation techniques, priming, etc. By low surface energy substrates is meant materials that have a surface energy of about 45 $mJ/m^2$ or less, more preferably about 40 $mJ/m^2$ or less and most preferably about 35 $mJ/m^2$ or less. Included among such materials are polyethylene, polypropylene, acrylonitrile-butadiene-styrene, polyamides, syndiotactic polystyrene, olefin containing block co-polymers, and fluorinated polymers such as polytetrafluoroethylene (Teflon™) which has a surface energy of less than about 20 $mJ/m^2$. (The expression "surface energy" is often used synonymously with "critical wetting tension" by others.) Other polymers of somewhat higher surface energy that may be usefully bonded with the compositions of the invention include polycarbonate, polymethylmethacrylate, and polyvinylchloride.

The polymerizable compositions utilizing amido-borates of the invention can be easily used as two-part adhesives. The components of the polymerizable compositions are blended as would normally be done when working with such materials. The liberating compound for the amido-borate is usually included with the free radical polymerizable component so as to separate it from the amido-borate, thus providing one-part of the two-part composition. The amido-borates of the polymerization initiator system provides the second part of the composition and are added to the first part shortly before it is desired to use the composition. Similarly, the Lewis acid catalyst where used for the heterocyclic ring opening compound polymerization is kept separate from the heterocyclic ring opening compound. The Lewis acid catalyst may be added to the first part directly or it may be pre-dissolved in an appropriate carrier such as a reactive olefinic monomer, i.e., methyl methacrylate or a methyl methacrylate/polymethylmethacrylate viscous solution.

The adhesive compositions may be used to bond two or more substrates together by contacting the parts of the composition together, contacting one of the substrates with the adhesive composition, contacting the substrates with the adhesive composition disposed between the substrates and allowing the adhesive composition to cure. In another embodiment, the invention is a laminate which comprises two or more substrates having the cured composition of the invention disposed between the substrates. The cured adhesive composition contains the residue of the organoborane derived from the amido-borate as described herein.

Preferably, the mixed two-part compositions have a suitable viscosity to allow application without dripping. Preferably, the viscosities of the two individual components should be of the same order or magnitude. Preferably, the mixed compositions have the viscosity of about 100 (0.1 Pa·S) centipoise or greater, more preferably about 5,000 (5.0 Pa·S), centipoise or greater and most preferably about 10,000 (10.0 Pa·S) centipoise or greater. Preferably, the adhesive compositions have a viscosity of about 500,000 (500 Pa·S) centipoise or less, more preferably 150,000 (150 Pa·S) centipoise or less, even more preferably about 100,000 (100 Pa·S) centipoise or less and most preferably about 50,000 (50 Pa·S) centipoise or less. Viscosity as used in this section is measured using a Brookfield viscometer according to ASTM D2196 using the conditions of a number 7 spindle, 20 RPM and 25° C.

Specific Embodiments

The following examples are included for illustrative purposes only and are not intended to limit the scope of the claims. Unless otherwise stated all parts and percentages are by weight.

Ingredients

The following ingredients were used in the examples provided hereinafter:

methyl methacrylate available from Rohm and Haas;

poly(methylmethacrylate) (270,000 mw) available from Rohm America Inc. under the trademark and designation, DEGALON LP51/07;

poly(methylmethacrylate) 996,000 mw available from Aldrich;

fumed silica available from Cabot Corporation under the trademark and designation Cab-O-Sil™ TS-720;

acrylic acid available from Sigma Aldrich;

Paraloid™ BTA 753 (ER) methacrylate-butadiene-styrene and copolymer, available from Rohm & Haas Company;

Hypalon™ 20 chlorosulfonated polyethylene available from Dupont-Dow Elastomers;

Scotchlite™ VS5500 glass bubbles available from 3M.

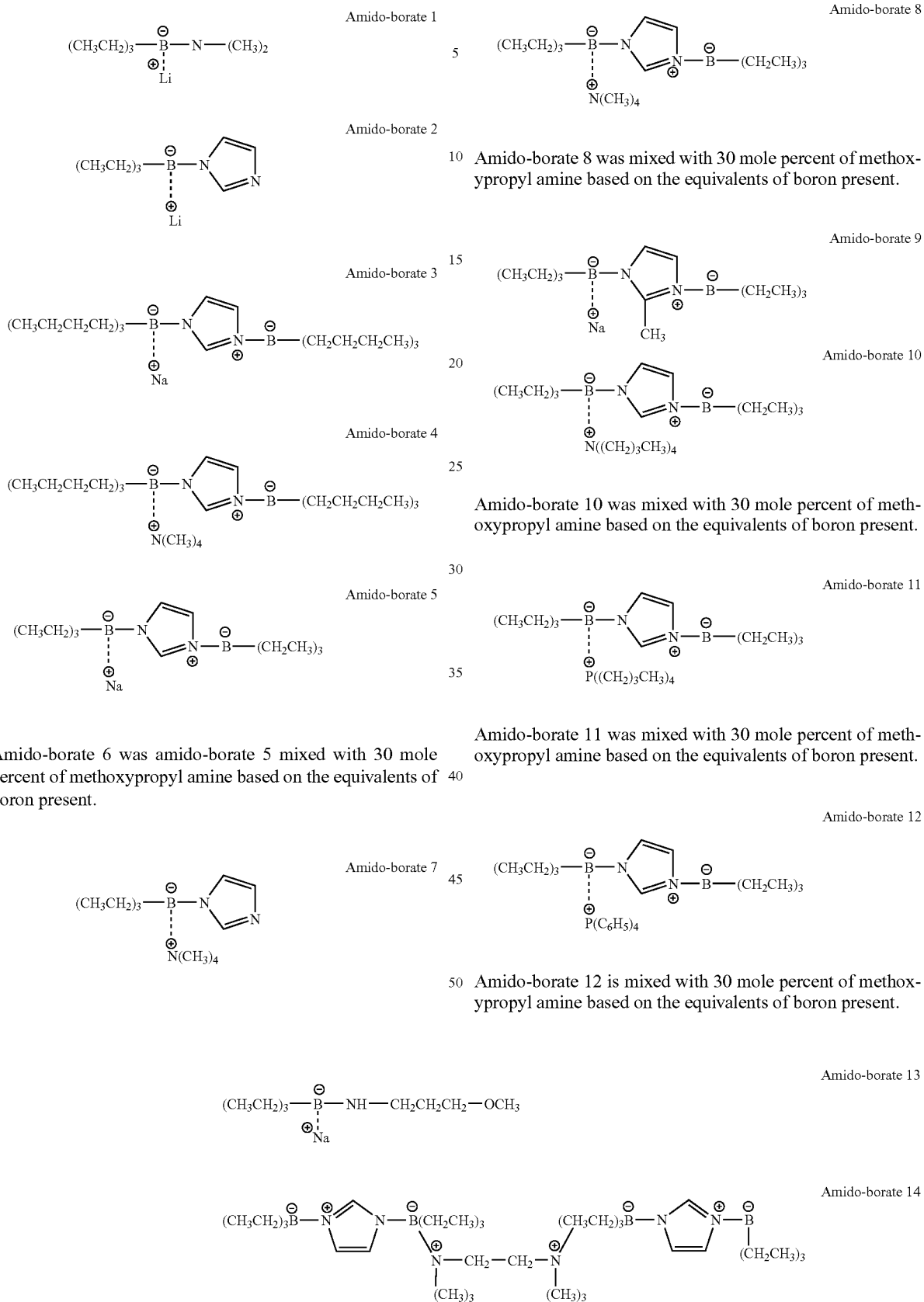

Amido-borate 14 is mixed with 30 mole percent of methoxypropyl amine based on the equivalents of boron present.

Synthesis of Amido-Borates

It is understood that the present invention is operable in the absence of any component which has not been specifically disclosed. Unless stated to the contrary, all parts and percentages are expressed on a weight basis. The term "overnight", if used, refers to a time of approximately 16-18 hours, "room temperature", if used, refers to a temperature of about 20-25° C.

All reagents were purchased from Aldrich and all solvents were purified using the technique disclosed by Pangborn et al, *Organometallics,* 15, 1518-1520, (1996). All compounds, solutions and reactions were handled under an inert atmosphere (dry box). $^1$H and $^{13}$C NMR shifts were referenced to internal solvent resonances and are reported relative to TMS.

Example 1

Preparation of Amido-borate 1 Lithium Dimethylamidotriethylborate

To a slurry of the solid, lithium dimethylamide (2.55 g, 50 mmol) in 30 mL of THF was added triethylborane (4.90 g, 50 mmol) slowly via syringe and the resulting mixture was stirred for 5 hours at room temperature. The solvent was removed in vacuo to afford a white solid. The crude product was further washed with hexane and dried under vacuum for 2 hours to give the desired product (86 percent yield).

Spectroscopic data are as follows: $^1$H NMR ($C_6D_6$, 23° C.): δ 3.89 (s br, 6H), 1.90 (t, 9H, $CH_2Me$), 0.42 (q, 6H, $CH_2Me$).

Preparation of Amido-Borate 5

To a slurry of the solid, sodium salt of imidazole (4.5 g, 50 mmol) in 30 mL of THF was added triethylborane (9.80 g, 100 mmol) slowly via syringe over 45 minutes and the resulting mixture was stirred overnight at room temperature. The solvent was removed in vacuo to afford brown oil. The crude product was used without further purification (98 percent yield).

Preparation of Amido-Borate 8

To a slurry of sodium salt of imidazole (9.006 g, 100 mmol) and tetramethylammonium chloride (10.96 g, 100 mmol) in 200 mL of THF was added triethylborane (19.6 g, 200 mmol) slowly via syringe over 60 minutes and the resulting mixture was stirred overnight at room temperature.

The salts formed were filtered and washed with 25 mL of THF twice. The solvent of the filtrate was removed in vacuo to afford the desired product as brown oil. The crude product was used without further purification (88 percent yield).

Preparation of Amido-Borate 9

To a slurry of the solid, sodium salt of 2-methylimidazole (5.205 g, 50 mmol), prepared by reacting 2-methylimidazole with stoichiometric amount of NaH in THF, in 30 mL of THF was added triethylborane (9.81 g, 100 mmol) slowly via syringe over 45 minutes and the resulting mixture was stirred overnight at room temperature. The solvent was removed in vacuo to afford brown oil (14.35 g, 95.6 percent yield). The crude product was used without further purification.

Preparation of Amido-Borate 10

To a slurry of sodium salt of imidazole (9.006 g, 100 mmol) and tetrabutylammonium chloride (27.90 g, 100 mmol) in 200 mL of THF was added triethylborane (19.6 g, 200 mmol) slowly via syringe over 60 minutes and the resulting mixture was stirred overnight at room temperature. The salts formed were filtered and washed with 25 mL of THF twice. The solvent of the filtrate was removed in vacuo to afford the desired product as brown oil (43.9 g, 86.7 percent).

Preparation of Amido-Borate 11

To a slurry of sodium salt of imidazole (9.006 g, 100 mmol) and tetrabutylphosphonium bromide (34.1 g, 100 mmol) in 200 mL of THF was added triethylborane (19.6 g, 200 mmol) slowly via syringe over 60 minutes and the resulting mixture was stirred overnight at room temperature. The salts formed were filtered and washed with 25 mL of THF twice. The solvent of the filtrate was removed in vacuo to afford the desired product as brown oily solids. The crude product was used without further purification (46.6 g, 89.1 percent yield).

Preparation of Amido-Borate 12

To a slurry of sodium salt of imidazole (4.5 g, 50 mmol) and tetraphenylphosphonium bromide (21 g, 50 mmol) in 200 mL of THF was added triethylborane (9.8 g, 100 mmol) slowly via syringe over 60 minutes and the resulting mixture was stirred overnight at room temperature. The salts formed were filtered and washed with 25 mL of THF twice. The solvent of the filtrate was removed in vacuo to afford the desired product as brown solids. The crude product was used without further purification (27.47 g, 91.2 percent yield).

Preparation of Amido-Borate 13

To a solution of triethylborane (4.9 g, 50 mmol) in 30 mL of THF was added 3-methoxypropylamine (4.5 g, 50.5 mmol) slowly via syringe over 15 minutes and then sodium hydride (1.22 g, 50.8 mmol) was added to the resulting mixture. The slurry was then gently refluxed over night. The solvent was removed in vacuo to afford an off white solid which was washed with hexanes and dried (9.32 g, 89.1 percent yield). The crude product was used without further purification.

Preparation of Amido-Borate 14

To a slurry of sodium salt of imidazole (4.5 g, 50 mmol) and hexamethyl-1,2-ethanediaminium diiodide (10.1 g, 25.2 mmol), prepared by reacting tetramethyl ethylenediamine with excess of methyl iodide, in 200 mL of THF was added triethylborane (9.8 g, 100 mmol) slowly via syringe over 60 minutes and the resulting mixture was stirred overnight at room temperature. The salts formed were filtered and washed with 25 mL of THF twice. The solvent of the filtrate was removed in vacuo to afford the desired product as brown solids. The crude product was used without further purification (13.3 g, 79.2 percent yield).

Preparation of Adhesive Compositions

Two part formulations were prepared by mixing the ingredients for each part, which were then placed in separate containers. Several different part B (hardener side) formulations were made.

Part A-Resin

The following ingredients were added to a 1 gallon (3.79 liters) metal can and rolled on a ball roll mill for 24 to 72 hours. For amido-borates 1 to 8, the ingredients were 63 parts of methyl methacrylate, 18 parts of polymethyl methacrylate (270,000 mw), and 5 parts of chlorosulfonated polyethylene (Hypalon™20 mw). 86 parts of the blended ingredients were added to an 8 oz. (236 mL) plastic cup. The ingredients were completely mixed by hand using a tongue depressor for 3 minutes. Two parts of glass bubbles and two parts of fumed silica were added and the ingredients were completely mixed by hand using a tongue depressor for 3 minutes. Ten parts of acrylic acid were added and the ingredients were completely mixed by hand using a tongue depressor for 3 minutes. The resulting mixture is packaged in an 8 oz. (236 mL) plastic cup.

For amido-borates 9 to 14, the ingredients were 58.7 parts of methyl methacrylate, 16.3 parts of methacrylate-butadiene-styrene copolymer, 15.2 parts of chlorosulfonated chloro polyethylene 0.25 parts of methyl ether of hydroquinone and 9.5 parts of methacrylic acid. All resin formulations were mixed using a dual asymmetric centrifugal FlackTek Speed-Mixer™ DAC 400 FVZ by Hauschild Engineering. The chlorinated polyethylene was combined with methyl methacrylate (MMA) into a preblend in a 40 percent chlorosulfonated chlorinated polyethylene to 60 percent MMA ratio using a roller mill. The chlorosulfonated chlorinated polyethylene MMA preblend was added to a speed mixing cup followed by methyl methacrylate and methoxyphenol (MEHQ™). The methacrylate-butadiene-styrene copolymer was then added to the speed mixing cup and immediately incorporated with the other ingredients by hand using a tongue depressor. The speed mixing cup was placed into the speed mixer and mixed three times consecutively for one minute at a speed of 1,800 rpm.

Part B Hardener

For amido-borates 1 to 8, Part B (hardener side) comprised 633 parts of methyl methacrylate, 180 parts of poly(methylmethacrylate), 45 parts of styrene butadiene styrene block copolymers were placed in a half gallon paint can and rolled on a roller mill overnight. Once the polymers dissolved to a homogeneous blend, 85.8 parts were placed in an 8 oz. (236 mL) plastic container and 2 parts of fumed silica and 2 parts of glass beads were added and mixed by hand using a tongue depressor. Finally 10 parts of amido-borate were added to the container and mixed. For amido-borates 6 and 8, 30 mole percent of methoxy propyl amine, based on the moles of amido-borate present, was added to the hardener side. For amido-borates 9 to 14, Part B comprised 65 percent methyl methacrylate, 25 percent of methacrylate-butadiene-styrene copolymer, 0.25 percent of Irgastab™ FS301 FF which is Irgastab™ FS301 FF a mixture of oxidized bis(hydrogenated tallow alkyl) amines (Irgastab™ FS042) and tris(2,4-di-tert-butyl phenol)phosphate trademark of Ciba Specialty Chemicals and 10 parts of a complex of tri-n-butyl borane and methoxypropyl amine.

Several Part A formulations were prepared using the procedures described above. The formulations are described below in Table 1.

Adhesives as described above were tested for Lap shear strength according to ASTM D3165-91 on the substrates listed below at several times from application as listed below. The surface area covered and overlapping was 1 inch (2.54 cm) wide by ½ inch (1.27 cm) long. The bond thickness of 30 mil (0.76 mm) was maintained using 30 mil (0.76 mm) glass beads. The samples were pulled on an Instron 5500 at a rate of 0.5 inches (1.27 cm) per minute until failure and the stress at failure were recorded in pounds per square inch. The results are compiled in Table 1 below. The surfaces of the substrates were not pretreated. The samples were cured for 3 days at room temperature and tested at room temperature (about 23° C.). The polypropylene substrate was 30 percent long glass filled polypropylene available from the Dow Chemical Company under the designation, DLGF 9310.00Z (30 percent long glass fiber filled). The e-coat substrate is ACT cold roll steel, ED 6100 from ACT Laboratories, Inc., Hillsdale, Mich. Relative to the mode of failure: Cohesive failure means that the break occurred in the adhesive; and Adhesive failure means the adhesive pulled away from the substrate. Substrate failure means that the substrate broke before the adhesive bond failed or the broke cohesively; and SD stands for substrate delamination, and it means a layer of the substrate was pulled off. The viscosities or some of the formulations were tested according to the procedure ASTM D2196 Brookfield viscometer, 20 rpm, and spindle number 7 at 25° C. The results are compiled in the Table.

| Amido-borate | PP Break Load lbf(N) | PP Break psi (MPa) | Failure mode | E-Coat Break Load lbf(N) | E-Coat Break psi (MPa) | Failure mode |
|---|---|---|---|---|---|---|
| 1 | 178 (792) | | adhesive | | | |
| 2 | 504 (2242) | | substrate | | | |
| 3 | 495 (2209) | | substrate | | | |
| 4 | 409 (1819) | 817 (5.63) | Adhesive/SD | 706.3 (3140) | 1413 (9.74) | cohesive |
| 5 | 308 (1370) | 615 (4.24) | Adhesive/SD | 518 (2304) | 1036 (7.14) | cohesive |
| 6 | 557 (2478) | 1114 (7.68) | substrate | 806 (3585) | 1611 (11.1) | cohesive |
| 7 | 551 (2451) | 1102 (7.60) | substrate | 1025 (4559) | 2049 (31.4) | cohesive |
| 8 | 279 (1241) | 557 (3084) | cohesive/ | 230 (1023) | 459 (7.05) | cohesive/ not cured |
| 9 | N/A | 10.52 (7.2) 53 | substrate | N/A | 15.88 (10.95) | cohesive |
| 10 | N/A | 781 (5.38) | thin film cohesive | N/A | 1215 (8.377) | cohesive |
| 11 | N/A | 803 (5.54) | thin film cohesive | N/A | 1527 (10.53) | cohesive |
| 12 | N/A | 500 (3.45) | adhesive | N/A | 1712 (11.80) | cohesive |
| 13 | N/A | 864 (5.96) | substrate | N/A | 1625 (11.20) | cohesive |
| 14 | N/A | 1040 (7.171) | substrate | N/A | 1373 (9.467) | cohesive |

SD means substrate delamination. PP means polypropylene is the substrate.
E-Coat means that the substrate is an e-coated metal panel.

The examples illustrate that the amido-borates are capable of ring acrylic adhesives and bonding to low energy substrates.

What is claimed is:

1. An amido-borate compound which corresponds to one of the formulas:

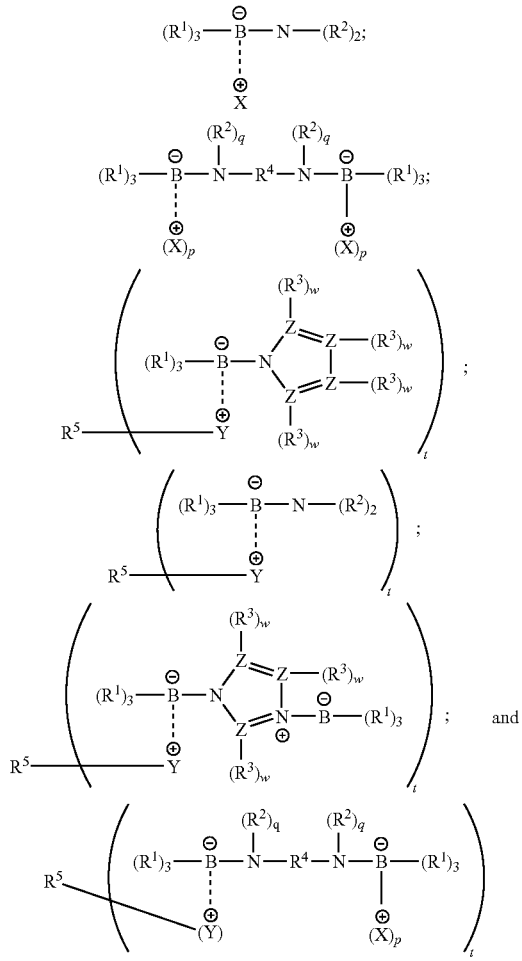

R$^1$ is independently in each occurrence an alkyl or cycloalkyl group, or two or more of R$^1$ may combine to form a cycloaliphatic ring;

R$^2$ is independently in each occurrence an alkyl, cycloalkyl, aryl, alkaryl, or aralkyl group containing one or more heteroatoms;

R$^3$ is independently in each occurrence hydrogen, an alkyl or an aryl group which may optionally contain one or more heteroatoms;

R$^4$ is independently in each occurrence a divalent hydrocarbyl moiety which may optionally contain one or more heteroatoms;

R$^5$ is independently in each occurrence a t-valent hydrocarbyl group;

X is independently in each occurrence a cation;

Y is independently in each occurrence

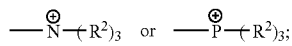

Z is independently in each occurrence N, P, Si or C;
p is independently in each occurrence 0 or 1;
q is independently in each occurrence 1 or 2;

with the proviso that the sum of p and q on each linked boron and nitrogen pair is 2 and the sum of the p and q is 1 or 2; where q is 2 the nitrogen to which it is bonded is quaternary and carries a positive charge which balances the negative charge found on the boron of the borate and a cation is not needed to neutralize the borate;

t is independently in each occurrence 2 or greater; and
w is independently in each occurrence either 0 or 1.

2. Compounds according to claim 1 wherein:

R$^1$ is independently in each occurrence a C$_{1-10}$ alkyl, C$_{3-10}$ cycloalkyl or two or more of R$^1$ may combine to form a cycloaliphatic ring;

R$^2$ is independently in each occurrence C$_{1-10}$ alkyl, C$_{3-10}$ cycloalkyl, C$_{6-12}$ aryl, C$_{7-20}$ alkaryl or C$_{7-20}$ aralkyl wherein such groups contain one or more heteroatoms of O or S, or an O or S containing functional moieties;

R$^3$ is independently in each occurrence hydrogen C$_{1-10}$ alkyl, C$_{3-20}$ cycloalkyl, C$_{6-20}$ aryl, C$_{7-20}$ alkaryl, C$_{7-20}$ aralkyl optionally containing one or more heteroatoms or heteroatom containing functional moieties;

R$^5$ is independently in each occurrence a t-valent alkylene group;

X is independently in each occurrence is an onium or an alkali metal ion;

Y is independently in each occurrence

Z is independently in each occurrence is N or C; and
t is 2 or 3.

3. Compounds according to claim 2 wherein:

R$^1$ is independently each in occurrence C$_{1-4}$ alkyl;

R$^2$ is independently in each occurrence C$_{1-10}$ alkoxyalkyl;

R$^3$ is independently in each occurrence hydrogen, C$_{1-4}$ alkyl or C$_{1-10}$ alkoxyalkyl;

R$^4$ is independently in each occurrence C$_{2-20}$ alkylene or C$_{2-20}$ alkylene containing one or more oxygen atoms;

R$^5$ is independently in each occurrence a t-valent, C$_{2-6}$ alkylene moiety;

X is an ammonium, phosphonium, sodium or lithium ion; and t is 2.

4. Compounds according to claim 3 wherein:

R$^1$ is independently in each occurrence C$_{2-4}$ alkyl;

R$^2$ is independently in each occurrence methoxy propyl, alkoxypropyl or propoxypropyl;

R$^3$ is independently in each occurrence hydrogen, methyl, ethyl or propyl;

R$^4$ is independently in each occurrence C$_{2-4}$ alkylene;

R$^5$ is a divalent C$_{2-4}$ alkylene group, and

X is tetraethyl ammonium, tetraethyl phosphonium, tetraphenyl phosphonium, sodium or lithium.

5. Compounds according to claim 1 which correspond to one of the formulas:

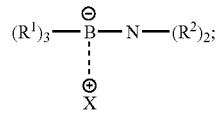

-continued

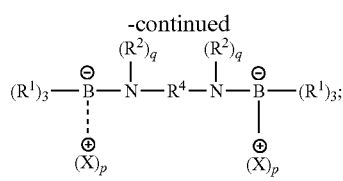

wherein;
R¹ is independently in each occurrence an alkyl or cycloalkyl group, or two or more or R¹ may combine to form a cycloaliphatic ring;
R² is independently in each occurrence an alkyl, cycloalkyl, aryl, alkaryl, or aralkyl group containing one or more heteroatoms or heteroatom containing functional moieties;
R³ is independently in each occurrence hydrogen, an alkyl or an aryl group which may optionally contain one or more heteroatoms or heteroatom containing functional moieties;
R⁴ is independently in each occurrence a divalent hydrocarbyl moiety which may optionally contain one or more heteroatoms or heteroatom containing functional moieties;
X is independently in each occurrence a cation;
Z is independently in each occurrence N, P, Si or C;
p is independently in each occurrence 0 or 1;
q is independently in each occurrence 1 or 2;
with the proviso that the sum of p and q on each linked boron and nitrogen pair is 2 and the sum of the p and q is 1 or 2 wherein q is 2, the nitrogen atom is the cation counter-balancing the borate anion;
w is independently in each occurrence either 0 or 1.

6. Amido-borates according to claim 1 which correspond to one of the formulas:

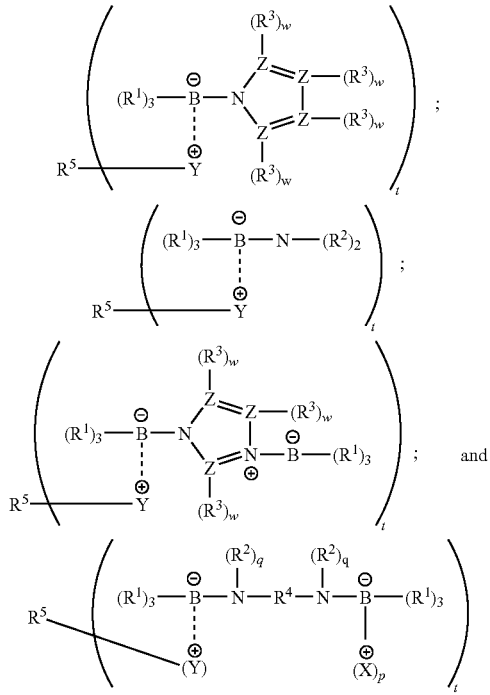

R¹ is independently in each occurrence an alkyl or cycloalkyl group, or two or more of R¹ may combine to form a cycloaliphatic ring;
R² is independently in each occurrence an alkyl, cycloalkyl, aryl, alkaryl, or aralkyl group containing one or more heteroatoms or heteroatom containing functional moieties;
R³ is independently in each occurrence hydrogen, an alkyl or an aryl group which may optionally contain one or more heteroatoms or heteroatom containing functional moieties;
R⁴ is independently in each occurrence a divalent hydrocarbyl moiety which may optionally contain one or more heteroatoms or heteroatom containing functional moieties;
R⁵ is independently in each occurrence a t-valent hydrocarbylene group optionally containing one or more heteroatoms or heteroatom containing functional moieties;
X is independently in each occurrence a cation;
t is independently in each occurrence 2 or greater;
Y is independently in each occurrence

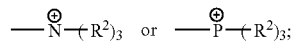

Z is independently in each occurrence N, P, Si or C;
p is independently in each occurrence 0 or 1;
q is independently in each occurrence 1 or 2;
with the proviso that the sum of p and q on each linked boron and nitrogen pair is 2; and
w is independently in each occurrence either 0 or 1.

7. Compounds according to claim 6 wherein:
R¹ is independently in each occurrence a $C_{1-10}$ alkyl, $C_{3-10}$ cycloalkyl or two or more of R¹ may combine to form a cycloaliphatic ring;
R² is independently in each occurrence $C_{1-10}$ alkyl, $C_{3-10}$ cycloalkyl, $C_{6-12}$ aryl, $C_{7-20}$ alkaryl or $C_{7-20}$ aralkyl wherein such groups contain one or more heteroatoms of O or S, or an O or S containing functional moieties;
R³ is independently in each occurrence hydrogen' $C_{1-10}$ alkyl, $C_{3-20}$ cycloalkyl, $C_{6-20}$ aryl, $C_{7-20}$ alkaryl, $C_{7-20}$ aralkyl optionally containing one or more heteroatoms or heteroatom containing functional moieties;
R⁵ is independently in each occurrence a t-valent alkylene group;
X is independently in each occurrence is an onium or an alkali metal ion;
Y is independently in each occurrence

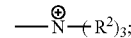

Z is independently in each occurrence is N or C; and
t is 2or 3.

8. Compounds according to claim 7 wherein:
R¹ is independently each in occurrence $C_{1-4}$ alkyl;
R² is independently in each occurrence $C_{1-10}$ alkoxyalkyl;
R³ is independently in each occurrence hydrogen, $C_{1-4}$ alkyl or $C_{1-10}$alkoxyalkyl;
R⁴ is independently in each occurrence $C_{2-20}$ alkylene or $C_{2-20}$ alkylene containing one or more oxygen atoms;
R⁵ is independently in each occurrence a t-valent, $C_{2-6}$ alkylene moiety;

X is an ammonium, phosphonium, sodium or lithium ion; and t is 2.

9. Compounds according to claim 8 wherein:
R$^1$ is independently in each occurrence C$_{2-4}$ alkyl;
R$^2$ is independently in each occurrence methoxypropyl, ethoxypropyl or propoxypropyl;
R$^3$ is independently in each occurrence hydrogen, methyl, ethyl or propyl;
R$^4$ is independently in each occurrence C$_{2-4}$ alkylene;
R$^5$ is a divalent C$_{2-4}$ alkylene group, and X is tetraethyl ammonium, tetraethyl phosphonium, tetraphenyl phosphonium; sodium or lithium.

10. An amido-borate corresponding to the formula $$(CH_3CH_2)_3 \overset{\ominus}{\underset{\overset{|}{\oplus Na}}{B}} - NH - CH_2 - CH_2 - CH_2 - OCH_3.$$

11. An amido-borate corresponding to the formula $$(CH_3CH_2)_3 \overset{\ominus}{B} - \overset{\oplus}{N} \overset{\frown}{\underset{\smile}{\phantom{N}}} N - \overset{\ominus}{B}(CH_2CH_3)_3 \qquad (CH_3CH_2)_3 \overset{\ominus}{B} - \overset{\oplus}{N} \overset{\frown}{\underset{\smile}{\phantom{N}}} N - \overset{\ominus}{B}(CH_2CH_3)_3.$$
$$\underset{(CH_3)_3}{\overset{\oplus}{N}} - CH_2 - CH_2 - \underset{(CH_3)_3}{\overset{\oplus}{N}}$$

\* \* \* \* \*